United States Patent [19]

Rustad

[11] Patent Number: 4,968,710
[45] Date of Patent: Nov. 6, 1990

[54] SUBSTITUTED DI-T-BUTYLPHENOLS AND ANTI-ALLERGIC USE THEREOF

[75] Inventor: Mark A. Rustad, St. Paul, Minn.

[73] Assignee: Riker Laboratories, Inc., St. Paul, Minn.

[21] Appl. No.: 248,586

[22] Filed: Sep. 26, 1988

Related U.S. Application Data

[63] Continuation-in-part of Ser. No. 120,468, Nov. 13, 1987, abandoned.

[51] Int. Cl.$^5$ .................... A61K 31/41; A61K 31/19; C07D 257/04; C07C 65/00
[52] U.S. Cl. .................................. 514/381; 514/532; 514/534; 514/568; 548/252; 562/432
[58] Field of Search ................ 548/252; 514/381, 568, 514/532, 534; 562/432; 560/17

[56] References Cited

U.S. PATENT DOCUMENTS

| | | | |
|---|---|---|---|
| 3,674,836 | 7/1972 | Creger | 260/473 |
| 4,675,334 | 6/1987 | Steggles et al. | 514/381 |
| 4,677,113 | 6/1987 | Bell et al. | 514/448 |
| 4,710,515 | 12/1987 | Kirk et al. | 514/563 |
| 4,714,776 | 12/1987 | Bell et al. | 562/460 |

FOREIGN PATENT DOCUMENTS

| | | |
|---|---|---|
| 0132367 | 1/1985 | European Pat. Off. . |
| 0181568 | 5/1986 | European Pat. Off. . |
| 0218872 | 4/1987 | European Pat. Off. . |
| 0235575 | 9/1987 | European Pat. Off. . |
| 50-39262 | 9/1985 | Japan . |
| 2143817A | 2/1985 | United Kingdom . |

Primary Examiner—David B. Springer
Attorney, Agent, or Firm—Donald M. Sell; Walter N. Kirn; Robert W. Sprague

[57] ABSTRACT

Novel compounds which are 2,6-di-t-butylphenols substituted in the 4 position by an alkoxy or benzyloxy group or a benzylthio group, which alkoxy or benzyloxy group is directly substituted by a tetrazole ring, and which benzylthio group is directly substituted by carboxy or tetrazolyl are useful as inhibitors of leukotriene biosynthesis and as antiallergic agents. Synthetic intermediates for preparing such compounds are also described.

23 Claims, No Drawings

SUBSTITUTED DI-T-BUTYLPHENOLS AND ANTI-ALLERGIC USE THEREOF

CROSS REFERENCE TO RELATED APPLICATION

This application is a continuation-in-part of copending application Ser. No. 120,468 which was filed Nov. 13, 1987, abandoned.

TECHNICAL FIELD

This invention relates to novel di-tertiary butyl phenols which exhibit antiallergic activity. Pharmaceutical compositions containing such compounds, pharmacological methods of using such compounds, and synthetic intermediates for preparing such compounds are also described.

BACKGROUND OF THE INVENTION

The leukotrienes are a novel group of biologically active mediators derived from arachidonic acid through the action of lipoxygenase enzyme systems. The leukotrienes are potent smooth muscle contracting agents, particularly on respiratory smooth muscle but also on other tissues. In addition, they promote mucous production, modulate vascular permeability changes and are potent inflammatory mediators in human skin. There are two groups of leukotrienes derived from the common unstable precursor Leukotriene $A_4$. The first of these are the peptido-lipid leukotrienes, the most important being Leukotrienes $C_4$ and $D_4$. These compounds collectively account for the biologically active material known as the slow reacting substance of anaphylaxis.

The most important compound in the second group of leukotrienes, namely dihydroxy fatty acids, is Leukotriene $B_4$. This compound is a potent chemotactic agent for neutrophils and eosinophils, and, in addition, may modulate a number of other functions of these cells. It also affects other cell types such as lymphocytes, and, for example, may modulate the action of suppressor cells and natural killer cells. When injected in vivo, in addition to promoting the accumulation of leukocytes, Leukotriene $B_4$ is also a potent hyperalgesic agent, and can modulate vascular permeability changes through a neutrophil dependent mechanism. Both groups of leukotrienes are formed following oxygenation of arachidonic acid through the action of a lipoxygenase enzyme. See, for example, D. M. Bailey et al., *Ann. Rpts. Med. Chem.*, 17, 203 (1982).

RESPIRATORY CONDITIONS

Asthma

The leukotrienes are potent spasmogens of human trachea, bronchus and lung parenchymal strips, and when administered to normal volunteers as aerosols, are 3,800 times more potent than histamine at inducing a 50% decrease in air flow at 30% of vital capacity. They mediate increases in vascular permeability in animals and promote mucous production in human bronchial explants. In addition, Leukotriene $B_4$ may also mediate mucous production, and could be an important mediator of neutrophil and eosinophil accumulation in asthmatic lungs. Lipoxygenase products are also thought to be regulators of mast cell degranulation, and recent studies with human lung mast cells have suggested that lipoxygenase inhibitors, but not corticosteroids, may suppress antigen-induced mast cell degranulation. In vitro studies have shown that antigen challenge of human lung results in the release of leukotrienes, and, in addition, purified human mast cells can produce substantial amounts of leukotrienes. There is, therefore, good evidence that the leukotrienes are important mediators of human asthma. Lipoxygenase inhibitors would, therefore, be a new class of drugs for the treatment of asthma. See, for example, B. Samuelsson, *Science*, 220, 568–575 (1983).

Psoriasis

Psoriasis is a human skin disease which affects between two and six percent of the population. There is no adequate therapy for psoriasis and related skin conditions. The evidence for leukotriene involvement in these diseases is as follows. One of the earliest events in the development of prepapillary lesions is the recruitment of leukocytes to the skin site. Injection of Leukotriene $B_4$ into human skin results in a pronounced neutrophil accumulation. There are gross abnormalities in arachidonic acid metabolism in human psoriatic skin. In particular, highly elevated levels of free arachidonic acid can be measured, as well as large amounts of lipoxygenase products. Leukotriene $B_4$ has been detected in psoriatic lesions, but not in uninvolved skin, in biologically significant amounts.

ALLERGIC CONDITIONS

Leukotrienes can be measured in nasal washings from patients with allergic rhinitis and are greatly elevated following antigen challenge. Leukotrienes may mediate this disease through their ability to regulate mast cell degranulation, by modulating mucous production and mucocillary clearance and by mediating the accumulation of inflammatory leukocytes.

Leukotrienes can also mediate other diseases. These include atopic dermatitis, gouty arthritis, gall bladder spasm and ulcerative colitis. In addition, they may have a role in cardiovascular disease because Leukotrienes $C_4$ and $D_4$ act as coronary and cerebral arterial vasoconstrictors, and these compounds may also have negative inotropic effects on the myocardium. In addition, the leukotrienes are important mediators of inflammatory disease through their ability to modulate leukocyte and lymphocyte function.

Japanese published application 50-39262 (published Sept. 5, 1985) to Toshiba discloses di-tertiarybutylphenol derivatives containing a subtituted benzylether or benzylthioether moiety. These compounds are said to exhibit antiarteriosclerosis and antilipaemia activity.

EP No. 0132367 to Eli Lilly and Company (published Jan. 30, 1985), EP No. 0181568 to USV Pharmaceutical Corporation (published May 21, 1986), and GB No. 2143817A to Lilly Industries Limited (published Feb. 20, 1985) all disclose antiallergic compounds containing an ether or thioether linkage.

No compounds wherein a 2,6-di-t-butylphenol is substituted in the 4-position by an alkoxy group wherein such alkoxy group is substituted by a tetrazole group are known. No compounds wherein a 2,6-di-t-butylphenol is substituted in the 4-position by a benzyloxy group wherein a tetrazole ring is bonded directly to the benzyl ring are known. No compounds wherein a 2,6-di-t-butylphenol is substituted in the 4-position by a benzylthio group wherein tetrazolyl or carboxy is bonded directly to the benzyl ring are known.

DETAILED DESCRIPTION OF THE INVENTION

The present invention relates to compounds of Formula I below:

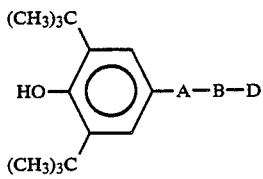   I wherein A is an oxygen or sulfur atom; B is a straight chain alkylene group of 3 to 8 carbon atoms or 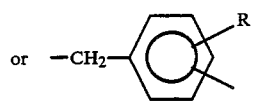

wherein R is hydrogen, halogen, or lower alkyl or lower alkoxy; and D is carboxy or tetrazolyl; with the proviso that when A is sulfur, B is

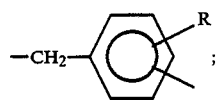 ;

with the further proviso that when A is oxygen, D is tetrazolyl; and derivatives of compounds wherein D is carboxy selected from the group consisting of lower alkyl esters, (lower)alkylamino(lower)alkyl esters, pharmaceutically acceptable lower(alkyl)amino(lower)alkyl ester addition salts and pharmaceutically acceptable carboxylate salts, and derivatives of compounds wherein D is tetrazolyl selected from pharmaceutically acceptable alkali metal and alkaline earth salts of the tetrazolyl moiety. This invention also relates to pharmacological methods for using such compounds and pharmaceutical formulations comprising such compounds.

This invention further relates to novel synthetic intermediates for preparing certain of the compounds of Formula I, which intermediates are of Formula IV below:

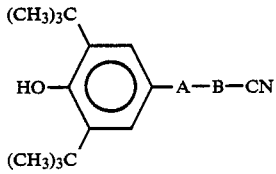   IV wherein A is an oxygen or sulfur atom; and B is a straight chain alkylene group of 3 to 8 carbon atoms or 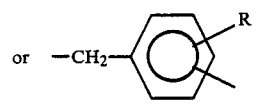

wherein R is hydrogen, halogen, lower alkyl or lower alkoxy; with the proviso that when A is sulfur, B is

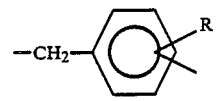

As used in the instant specification and claims, the term "lower" in connection with alkyl and alkoxy denotes alkyl and alkoxy groups containing 1 to about 4 carbon atoms in straight or branched-chain configuration.

In the compounds of Formula I, wherein D is tetrazolyl, two tautomeric forms of tetrazolyl exist as is known to those skilled in the art. Both tautomers are within the scope of this invention.

It is well known to the art that pharmaceutically acceptable salts such as alkali metal, alkaline earth, aluminum and other metal and amine salts of pharmaceutically active acids are the equivalents of the acids in terms of activity, and in some cases may even offer advantages in absorption, formulation and the like. Pharmaceutically-acceptable carboxylate salts of the compounds of the invention which contain carboxyl as D are prepared in an inert atmosphere by reaction of the acid with a base and subsequent evaporation to dryness, preferably under mild conditions. The base may be organic, e.g., sodium methoxide or an amine, or inorganic, e.g., sodium hydroxide. Alternatively, the cation of a carboxylate salt, e.g., sodium, may be displaced by a second cation such as calcium or magnesium when the salt of the second cation is more insoluble in a selected solvent.

Other useful derivatives of the compounds of the invention which contain carboxyl as D include alkyl esters, alkylaminoalkykl esters, and salts of the latter. In the ester derivatives, the hydrogen portion of the carboxylic acid group is replaced with an alkyl or substituted alkyl, preferably an alkylaminoalkyl group.

Esters of the compounds of the invention may be obtained as intermediates during the preparation of the acidic compound. In some cases, the esters may be prepared directly using standard synthetic methods. These esters may exhibit antiallergic activity, but they are primarily of interest as synthetic intermediates, although in some instances hydrolyzable or salt-forming esters may be of interest as therapeutic agents. Preferred esters are alkyl esters and alkylaminoalkyl esters having one to four carbon atoms in the alkyl group.

Ester derivatives may be obtained by alkylation of an alkali metal salt of the compound in dimethylformamide with an alkyl iodide or dialkylaminoalkylchloride, or by starting with esters instead of acids in Reaction Scheme II, Step (1) below.

Pharmaceutically acceptable alkali metal and alkaline earth salts may also be prepared of compounds of Formula I wherein D is tetrazolyl by methods known to those skilled in the art.

The preferred compounds of Formula I are 5-[6-(3,5-di-t-butyl-4-hydroxyphenoxy)hexyl]tetrazole and 4-[4-(3,5-di-t-butyl-4-hydroxyphenylthio)methyl tetrazole.

The compounds of the invention of Formula I wherein D is tetrazolyl may be prepared according to the method of Reaction Scheme I below wherein X is halogen and A and B are as defined above:

Reaction Scheme I

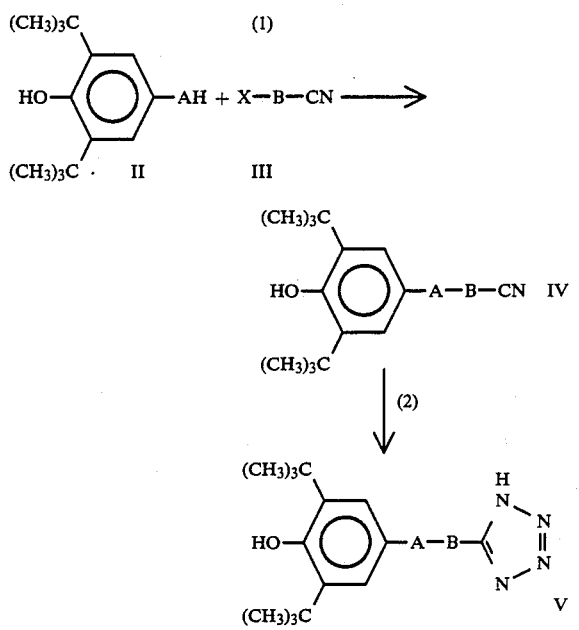

Reaction Scheme II

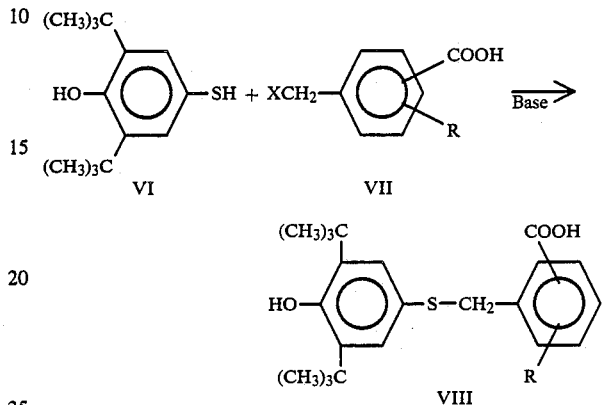

In step (1) of Reaction Scheme I, known 2,6-di-t-butyl-1,4-hydroquinone (Formula II wherein A is oxygen) is first converted to a salt by reacting it with a metal hydride such as sodium hydride or potassium hydride in the presence of a polar solvent such as N,N-dimethylformamide and then mixed with a solution containing 1.1 to 1.4 equivalents of a haloalkyl nitrile or a halobenzyl nitrile of Formula III in a polar solvent such as N,N-dimethylformamide. The reaction mixture is heated at 120° C. for 12 to 48 hours; alternatively, the reaction may be run without heating. Haloalkyl nitriles of Formula III are known compounds or may be prepared by known methods and include 7-bromoheptanenitrile, and the like. Cyanobenzylhalides of Formula III are also known compounds or may be prepared using known methods and include p-cyanobenzyl bromide. Alternatively, known 2,6-di-t-butyl-4-mercaptophenol (Formula II wherein A is sulfur) is combined with one equivalent of a halobenzyl nitrile of Formula III and one equivalent of a base such as sodium hydroxide in the presence of a polar solvent such as ethanol or N,N-dimethylformamide. The solution is then heated at reflux until thin layer chromatography shows that the reaction is complete. The intermediates of Formula IV are novel compounds which are readily isolated and may be purified, for example, by chromatography and/or recrystallization.

In step (2), the intermediate of Formula IV is combined with 3.0 to 6.0 equivalents of sodium azide, 3.0 to 6.0 equivalents of ammonium chloride, and 1.0 equivalent of lithium chloride in the presence of a polar solvent such as N,N-dimethylformamide. The reaction mixture is heated in a stoppered flask at 100°–120° C. for 12 to 140 hours. Alternatively, the intermediate of Formula IV is combined with about 1.5 equivalents of triethylammonium chloride and about 3 equivalents of sodium azide in the presence of 1-methylpyrrolidinone. The reaction mixture is heated under a nitrogen atmosphere at about 150° C. for 16 to 72 hours. The products of Formula V which is a subgenus of Formula I are readily isolated and may be purified, for example, by chromatography and/or recrystallization.

The compounds of the invention of Formula I wherein D is carboxy may be prepared according to the method of Reaction Scheme 11 below wherein X is halogen and R is as defined above:

In Reaction Scheme II, known 2,6-di-t-butyl-4-mercaptophenol (VI) is combined with one equivalent of an alpha-halo-toluic acid of Formula VII and two equivalents of a base such as potassium hydroxide in the presence of a polar solvent such as aqueous ethanol. Compounds of Formula VII are known compounds or may be prepared using known methods and include alpha-bromo-p-toluic acid. The reaction is heated at reflux until it is complete. The product of Formula VIII which is a subgenus of Formula I may be readily isolated and purified.

The activity of compounds of Formula I may be demonstrated readily by in vivo testing. The in vivo test used may be any of those known to those skilled in the art. Preferably, bronchoconstriction in sensitized guinea pigs is measured upon antigen challenge. Active compounds are those which demonstrate an intraperitoneal $ED_{40}$ of 100 mg per kg or less, and preferably an $ED_{40}$ of 50 mg per kg or less. Most preferred compounds are active at 25 mg per kg. This test is described in broad terms by Piechuta, et al., Immunology, 38, 385 (1979) and more specifically by Hammerbeck and Swingle, Int. Archs. Allergy Appl. Immun., 74, 84–90 (1984), both references being incorporated herein by reference. It is used in a modified form as follows: Male Hartley guinea pigs (250–600g) were pretreated with an antihistamine, e.g., chlorpheniramine, then dosed intraperitoneally with a compound of the invention at a level of about 1 to 40 mg/kg 15 minutes prior to challenge or orally at the same dose 30 minutes prior to challenge. The animals are placed under an inverted dessicator jar (18×14 cm) with a constant flow of air coming into the chamber from a compressed-air source to prevent hypoxia and were aerosol challenged with either water or ovalbumin at a concentration of 10 mg per ml. Air flow leaving the chamber and fluctuations due to respiration were monitored through a separate outlet with a Fleisch No. 0000 pneumotachograph (available from Beckman Instruments, Inc., Schiller Park, Ill.) coupled to a Beckman Type R dynograph (available from Beckman Instruments, Inc.). Aerosolization through a third outlet is made via a No. 4 DeVilbiss nebulizer (available from The DeVilbiss Company, Somerset, PA) for 90 seconds at 150 mm Hg. The characteristic respiratory patterns observed are summations of two air exchange processes occurring simultaneously in the chamber. One exchange process is due to inspiration and expiration of air into and out of the animal, while the other exchange process is due to the air flow into and out of the chamber due to respiratory movements. The tracing obtained is the mechanical representation of the summation of those flows. Superimposed on the tracings is a characteristic spiking ('notching'), which appears to be an exaggerated expiratory movement, the frequency of which correlates with the severity of the bronchoconstrictive reaction. The frequency of notching for 15-minute periods beginning 4 minutes after the beginning of the aerosol challenge is used for comparing various treatments. Effects are considered significant if the t value achieved $p<0.05$.

The compounds may also be tested in more specific tests for the inhibition of leukotriene synthesis. Active compounds are those which exhibit an $IC_{50}$ of 100 micromolar or less, and preferably less than 25 micromolar. Most preferred compounds exhibit an $IC_{50}$ of 10 micromolar or less. The compounds are tested in either intact cells or in cell sonicate. The intact cell assay is similar to that described by Verhagen et al., FEBS Letter 168, 23–28 (1984), incorporated herein by reference. Human leukocytes are prepared using standard procedures. The cells are incubated in pH 7.4 Tris buffer containing 1 millimolar calcium chloride. After vehicle or drug incubation, the cells are activated with the calcium ionophore A 23187 (4 micrograms per ml). After 10 minutes at room temperature, the cells are centrifuged and the supernatants are stored for assay of $LTC_4$ content by radioimmunoassay. The cell sonicate assay utilizes the cell free leukotriene biosynthesis system of M. Steinhoff et al., Biochim. Biophy. Acta., 68, 28 (1980), incorporated herein by reference which consists of homogenized rat basophil leukemia cells. Leukotriene synthesis is initiated by the addition of arachidonate. Solutions are centrifuged and supernatants assayed using a radioimmunoassay developed as described by Aeringhaus et al., FEBS Letter 146, 111–114, incorporated herein by reference. Drugs are dissolved in ethanol or dimethyl sulfoxide and preincubated for five minutes. Phenidone is used as a positive control.

The oral activity of the compounds of Examples 4 and 22 was demonstrated using the Konzett-Rossler in vivo test method. The activity was determined according to the procedure which follows. The Konzett-Rossler technique (H. Konzett and R. Rossler, Naunyn-Schmiedbergs Arch. Pharmakol., 195, 71–74 (1940), incorporated herein by reference, was used to assess the effect of compounds on antigen challenge of male Hartley strain guinea pigs (350–500g) Fourteen days after sensitization with ovalbumin (50 mg/kg intraperitoneally) guinea pigs were anesthetized with pentobarbital (70 mg/kg intraperitoneally) and spontaneous respiration was eliminated with succinylcholine (2 mg/kg intraperitoneally). The trachea was cannulated and respiration was maintained under positive pressure with a miniature ventilator (5 ml/breath, 87 breaths/minute, 10 cm water). Bronchoconstrictor responses were represented as increased excursions of the tracing on a physiological recorder of air overflow to the lungs measured by a pneumotachograph in series with a differential pressure transducer. The guinea pigs were pretreated with an antihistamine, for example, chlorpheniramine, and then dosed orally at a level of about 5 to 40 mg/kg with a solution of a compound in 0.1 N NaOH. The animals were challenged with ovalbumin (300 micro-g/kg intraveneously) thirty minutes later.

The pharmaceutical compositions of the present invention will contain sufficient compound of Formula I in a dosage form suitable for inhibiting the mammalian biosynthesis of leukotrienes, or for the treatment desired. The effective concentration of the Formula I compound in the composition will vary as required by the mode of administration, dosage form and pharmacological effect and level desired.

For treating pulmonary conditions such as asthma, the mode of administration may be oral, parenteral, by inhalation, by suppository and the like. Suitable oral dosage forms are tablets, elixirs, emulsions, solutions, capsules, including delayed or sustained release dosage forms. Dosage forms for administration by inhalation include aerosols and sprays and may be administered in metered dose.

For treating allergies or allergic reactions, the compound of Formula I may be administered by any conventional mode, e.g., orally, parenterally, topically, subcutaneously, by inhalation and the like. The oral and parenteral dosage forms are as described for pulmonary treatment. The topical application dosage forms include ointments, sprays, controlled release patches, powders, solutions and the like.

For treating inflammation, the mode of administration may be oral, parenteral, by suppository and the like. The various dosage forms are as described above.

For treating skin diseases such as psoriasis, atopic dermatitis and the like, oral, topical or parenteral administration is useful. For topical application to the diseased area, salves, patches, controlled release patches, emulsions, etc. are convenient dosage forms.

For treating cardiovascular conditions, any suitable mode of administration, such as oral or intraperitoneal, may be used.

In addition to the common dosage forms listed above, the compounds of Formula I may also be administered for various utilities and indications or for inhibiting leukotriene synthesis by controlled release means and/or delivery devices.

In preparing suitable dosage forms, conventional compounding procedures and ingredients, e.g., diluents, carriers, etc. may be used. Examples of suitable solid carriers are lactose, terra alba, sucrose, talc, gelatin, agar, pectin, acacia, magnesium stearate, stearic acid and the like. Examples of suitable liquid carriers are syrup, peanut oil, olive oil, PEG-400, water and the like. Similarly, the carrier or diluent can include any time delay material well known to the art, such as glyceryl monostearate or glyceryl distearate, these being useful alone or, for example, in combination with wax.

The following examples are provided to illustrate the invention, but are not intended to limit the invention.

EXAMPLE 1

Preparation of 2,6-Di-t-Butyl-4-[(4-cyanophenyl)methoxy]phenol

Under a nitrogen atmosphere, a solution of 11.2 g (0.05 mole) of 3,5-di-t-butyl-1,4-hydroquinone in 30 ml of N,N-dimethylformamide was added dropwise to a suspension of 2.4 g (0.06 mole) 60% sodium hydride in 25 ml of N,N-dimethylformamide, and a solution of 11.8 g (0.06 mole) of p-cyanobenzyl bromide in 20 ml of N,N-dimethylformamide was then added dropwise. The resulting mixture was heated at 120° C. for 48 hours. The reaction mixture was poured into water to give the crude product as a brown solid. This material was purified by silica gel chromatography eluting with 4% ethyl acetate in hexane followed by trituration of the isolated material with hexane and recrystallization from ethanol, to give 6.2 g of white 2,6-di-t-butyl-4-[(4-cyanophenyl)-methoxy]phenol m.p. 166°–169° C. Analysis: Calculated for $C_{22}H_{27}NO_2$: %C, 78.3; %H, 8.1; %N, 4.0; Found: %C, 78.7; %H, 8.1; %N, 4.0.

EXAMPLE 2

Preparation of 5-[4-(3,5-Di-t-Butyl-4-Hydroxyphenoxymethyl)-phenyl]tetrazole

A mixture of 1.68 g (5 mmole) of 2,6-di-t-butyl-4[(4-cyanophenyl)methoxy]phenol (from Example 1) 0.97 g (15 mmole) of sodium azide, 0.30 g (15 mmole) of ammonium chloride, 0.21 g (5 mmole) of lithium chloride and 25 ml of N,N-dimethylformamide was heated in a stoppered flask at 100° C. for 16 hours. The reaction mixture was poured into a mixture of ice and water, and was then extracted with chloroform. The chloroform extract was washed with water, dried and evaporated to give the crude product as an oil. The oil was triturated with water to give a solid. The solid was purified by silica gel chromatography eluting with a mixture of methanol/chloroform/acetic acid in a ratio of 5/94.5/0.5 followed by two recrystallizations from a mixture of methanol, chloroform and hexane to give 0.22 g of white 5-[4-(3,5-di-t-butyl-4-hydroxyphenoxymethyl)phenyl]tetrazole, m.p. 235°–237° C. Analysis: Calculated for $C_{22}H_{28}N_4O_2$: %C, 69.4; %H, 7.4; %N, 14.7; Found: %C, 69.0; %H, 7.6; %N, 14.6.

EXAMPLE 3

Preparation of 7-(3,5-Di-t-Butyl-4-Hydroxyphenoxy)heptanenitrile

Under a nitrogen atmosphere, a solution of 11.2 g (0.05 mole) of 3,5-di-t-butyl-1,4-hydroquinone in 30 ml of N,N-dimethylformamide was added dropwise to a suspension of 2.4 g (0.06 mole) 60% sodium hydride in 25 ml of N,N-dimethylformamide over a period of 10 minutes. A solution of 11.4 g (0.06 mole) of 7-bromoheptanenitrile in 20 ml of N,N-dimethylformamide then was added, and the resulting mixture was heated at 120° C. for 48 hours. The reaction mixture was poured into water and the mixture was extracted with hexane. The hexane extract was washed with water, and then dried and evaporated to give the crude product as an oil. This oil was purified twice by silica gel chromatography eluting with a mixture of ethyl acetate and hexane to give 7-(3,5-di-t-butyl-4-hydroxyphenoxy)heptanenitrile as an oil. The structure was confirmed by infrared and nuclear magnetic resonance spectral analysis.

EXAMPLE 4

Preparation of 5-[6-(3,5-Di-t-Butyl-4-Hydroxyphenoxy)hexyl]tetrazole

A mixture of 4.0 g (12.1 mmole) of 7-(3,5-di-t-butyl-4-hydroxyphenoxy)heptanenitrile (from Example 3), 2.35 g (36.2 mmole) sodium azide, 1.94 g (36.2 mmole) of ammonium chloride, 0.51 g (12.1 mmole) of lithium chloride and 50 ml of N,N-dimethylformamide was heated in a stoppered flask at 120° C. for 48 hours. To this mixture was added 2.35 g (36.2 mmole) of sodium azide and 1.94 g (36.2 mmole) of ammonium chloride, and heating was continued for an additional 48 hours. The reaction mixture was poured into water and extracted twice with chloroform. The chloroform extracts were combined, washed with water, dried with magnesium sulfate and evaporated to give the crude product as a dark oil. This oil was purified by four recrystallizations from a mixture of ethyl acetate and hexane, followed by silica gel chromatography eluting with a mixture of chloroform/methanol/acetic acid in a ratio of 98/2/0.25. After three further recrystallizations, 0.92 g of 5-[6-(3,5-di-t-butyl-4-hydroxyphenoxy)hexyl]-tetrazole, m p. 128°–131° C., was obtained as a white solid. Analysis: Calculated for: $C_{21}H_{34}N_4O_2$: %C, 67.4; %H, 9.2; %N, 15.0; Found: %C, 67.4; %H, 9.3; %N, 15.2.

EXAMPLE 5

Preparation of 2,6-Di-t-Butyl-4-[(2-Cyanophenyl)methoxy]phenol

Under a nitrogen atmosphere, a solution of 11.2 g (0.05 mole) of 3,5-di-t-butyl-1,4-hydroquinone in 30 ml of N,N-dimethylformamide was added dropwise to a suspension of 2.4 g (0.06 mole) of 60% sodium hydride in 25 ml of N,N-dimethylformamide. The resulting mixture was allowed to stir for 30 minutes, and a solution of 11.8 g (0.05 mole) of 2-cyanobenzyl bromide in 20 ml of N,N-dimethylformamide was added and the reaction was heated at 120° C. for 16 hours. The reaction mixture was poured into water, acidified with 5% hydrochloric acid, and extracted with ethyl acetate. The ethyl acetate extract was washed with water, dried with magnesium sulfate and evaporated to give the crude product as an oil. The oil was purified by silica gel chromatography eluting with 2% ethyl acetate in hexane, followed by recrystallization from a mixture of ethyl acetate and hexane to give 9.1 g of 2,6-di-t-butyl-4-[(2-cyanophenyl)methoxy]phenol as a white solid, m.p. 117°–119° C. Analysis: Calculated for $C_{22}H_{27}NO_2$; %C, 78.3; %H, 8.1; %N, 4.1; Found: %C, 78.1; %H, 8.0; %N, 4.0.

EXAMPLE 6

Preparation of 4-(3,5-Di-t-Butyl-4-Hydroxyphenoxy)butyronitrile

Under a nitrogen atmosphere, a solution of 11.2 g (0.05 mole) 3,5-di-t-butyl-1,4-hydroquinone in 30 ml of N,N-dimethylformamide was added dropwise to a suspension of 2.4 g (0.06 mole) of 60% sodium hydride in 25 ml of N,N-dimethylformamide over a period of 10 minutes. A solution of 8.9 g (0.06 mole) of 4-bromobutyronitrile in 20 ml of N,N-dimethylformamide then was added and the resulting mixture was heated at 120° C. for 48 hours. The reaction mixture was poured into water and extracted with 20% ethyl acetate in hexane. The extract was washed with water, and was dried and evaporated to give a brown oil. This oil was purified by two silica gel chromatographies eluting with a mixture of ethyl acetate and hexane followed by a recrystallization from hexane to give 2.5 g of 4-(3,5-di-t-butyl-4-hydroxyphenoxy)butyronitrile as a tan solid, m.p. 67°–69° C. Analysis: Calculated for $C_{18}H_{27}NO_2$; %C, 74.7; %H, 9.4; %N, 4.8; Found: %C, 75.0; %H, 9.7; %N, 4.7.

EXAMPLE 7

Preparation of 2,6-Di-t-Butyl-4-[(3-Cyanophenyl)methoxy]phenol

Under a nitrogen atmosphere, a solution of 11.2 g (0.05 mole) of 3,5-di-t-butyl-1,4-hydroquinone in 30 ml of N,N-dimethylformamide was added dropwise to a suspension of 2.4 g (0.06 mole) of 60% sodium hydride in 25 ml of N,N-dimethylformamide. The resulting mixture was stirred for 50 minutes, and a solution of 11.8 g (0.05 mole) 3-cyanobenzyl bromide in 30 ml of N,N-dimethylformamide was added. The reaction mixture was stirred at 120° C. for 16 hours. The reaction mixture was poured into cold water, acidified with 5% hydrochloric acid and extracted with ethyl acetate. The ethyl acetate extract was washed with water, dried with magnesium sulfate and evaporated to give the crude product as an oil. This oil was purified by silica gel chromatography eluting with 2% ethyl acetate in hexane followed by recrystallization from a mixture of ethyl acetate and hexane to give 2.43 g of 2,6-di-t-butyl-4-[(3-cyanophenyl)methoxy]phenol as a white solid, m.p. 78°–81° C. Analysis: Calculated for $C_{22}H_{27}NO_2$; %C, 78.3; %H, 8.1; %N, 4.1; Found: %C, 78.3; %H, 8.1; %N, 4.1.

EXAMPLE 8

Preparation of 5-[2-(3,5-Di-t-Butyl-4-hydroxyphenoxymethyl)phenyl]-tetrazole Under a nitrogen atmosphere a mixture of 4.00 g (0.012 mole) of 2,6-di-t-butyl-4-[(2cyanophenyl)methoxy]phenol, 2.45 g (0.018 mole) of triethylamine hydrochloride, 2.32 g (0.036 mole) of sodium azide and 200 ml of 2-methylpyrrolidinone was heated at 150° C. for about 48 hours. The reaction mixture was poured into a mixture of water and ice and then extracted six times with 75 ml portions of diethyl ether. The diethyl ether extracts were combined, washed with water and brine, dried over magnesium sulfate and then evaporated to provide a yellow orange oil. The oil was purified by silica gel chromatography eluting with 1:1 acetone:hexane containing 3 ml of acetic acid per 2000 ml of solvent, followed by recrystallization from a mixture of ethyl acetate and hexane to give 2.76 g of a solid. This material was recrystallized from a mixture of ethyl acetate and hexane to provide 1.44 g of 5-[2-(3,5-di-t-butyl-4-hydroxyphenoxymethyl)phenyl]tetrazole, m.p. 149°–150.5° C. Analysis: Calculated for $C_{22}H_{28}N_4O_2$, %C, 69.4; %H, 7.4; %N, 14.7; Found: %C, 69.5; %H, 7.4; %N, 14.9.

EXAMPLE 9

Preparation of 5-[3-(3,5-Di-t-butyl-4-hydroxyphenoxy)propyl]tetrazole

Under a nitrogen atmosphere a mixture of 8.66 g (0.030 mole) of 4-(3,5-di-t-butyl-4-hydroxyphenoxy)-butyronitrile, 6.42 g (0.047 mole) of triethylammonium chloride, 5.79 g (0.089 mole) of sodium azide and 250 ml of 1-methylpyrrolidinone was heated about 150° C. for about 72 hours. The reaction mixture was poured into water. The pH was adjusted to pH 1 with 10% hydrochloric acid and then the mixture was extracted eight times with 100 ml portions of diethyl ether. The diethyl ether extracts were combined, washed with brine, dried over magnesium sulfate and then evaporated to provide a yellow orange oil. The oil was purified by silica gel chromatography eluting with 2:1 hexane:acetone containing 3 ml of acetic acid per 2000 ml of solvent, followed by recrystallization from a mixture of ethyl acetate and hexane to provide 2.66 g of 5-[3-(3,5-di-t-butyl-4-hydroxyphenoxy)propyl]tetrazole as a white solid, m.p. 179°–180° C. Analysis: Calculated for $C_{18}H_{28}N_4O_2$, %C, 65.0; %H, 8.5; %N, 16.8; Found: %C, 65.3; %H, 8.5; %N, 16.8.

EXAMPLE 10

Preparation of 5-[3-(3,5-Di-t-Butyl-4-hydroxyphenoxymethyl)phenyl]-tetrazole Under a nitrogen atmosphere, a mixture of 2.15 g (0.006 mole) of 2,6-di-t-butyl-4-[(3-cyanophenyl)methoxy]phenol, 1.24 g (0.019 mole) of sodium azide, 1.32 g (0.010 mole) of triethylammonium chloride and 100 ml of 1-methylpyrrolidinone was heated at about 100° C. for about 16 hours and then allowed to stand at room temperature for about 60 hours. The reaction mixture was poured into water and acidified with 10% hydrochloric acid to provide a gummy solid. The solid was taken up in diethyl ether, washed with brine, dried by filtration through Whatman IPS paper and evaporated to provide a dark oil. The oil was purified by recrystallization from a mixture of ethyl acetate and hexane followed by silica gel chromatography eluting with 2:1 hexane:acetone containing a trace of acetic acid to provide 0.59 g of a pale blue crystalline solid. The blue solid was further purified by silica gel chromatography eluting with 1:1 acetone:hexane containing a trace of acetic acid to provide 0.2 g of 5-[3-(3,5-di-t-butyl-4-hydroxyphenoxymethyl)phenyl]tetrazole as a white solid, m.p. 163°–164.5° C. Analysis: Calculated for $C_{22}H_{28}N_4O_2$: %C, 69.4; %H, 7.4; %N, 14.7; Found: %C, 69.2; H, 7.4; %N, 14.6.

EXAMPLE 11

Preparation of 6-(3,5-Di-t-Butyl-4-hydroxyphenoxy)hexanenitrile

Under a nitrogen atmosphere, a solution of 10.0 g (0.045 mole) of 3,5-di-t-butyl-1,4-hydroquinone in 30 ml of N,N-dimethylformamide was added dropwise over a period of several hours to a suspension of 2.23 g (0.058 mole) of 60% sodium hydride in 20 ml of N,N-dimethylformamide. A solution of 10.2 g (0.058 mole) of 6-bromohexanenitrile in 5 ml of N,N-dimethylformamide was then added dropwise over a period of one hour. The resulting mixture was stirred at about 25° C. for about 60 hours and then at 120° C. for about 72 hours. The reaction mixture was poured into water and then extracted five times with 100 ml portions of hexane. The extracts were combined, washed twice with 100 ml portions of brine, dried by filtration through Whatman IPS paper and evaporated to provide 12.9 g of a red brown oil. This oil was purified twice by silica gel chromatography eluting the first time with 20% ethyl acetate in hexane and the second time with 10% ethyl acetate in hexane to provide 3.9 g of 6-(3,5-di-t-butyl-4-hydroxyphenoxy)hexanenitrile as an oil. The structure was confirmed by nuclear magnetic resonance spectral analysis.

EXAMPLES 12–14

Intermediate of Formula IV which could be prepared by the reaction of 3,5-di-t-butyl-1,4-hydroquinone with known starting materials using the general method of Example 1 are shown in Table I.

magnesium sulfate and evaporated to provide a yellow oil. This oil was purified by silica gel chromatography

TABLE I

| Example No. | Starting Material | Product |
|---|---|---|
| 12 | 4-BrCH₂, 1-CH₃, 3-CN benzene (CH₃ top, BrCH₂ left, CN bottom) | 3,5-di-t-butyl-4-hydroxyphenyl-O-CH₂-(4-methyl-3-cyanophenyl) |
| 13 | 4-BrCH₂, 1-OCH₃, 3-CN benzene | 3,5-di-t-butyl-4-hydroxyphenyl-O-CH₂-(4-methoxy-3-cyanophenyl) |
| 14 | 3-BrCH₂, 1-Cl, 4-CN benzene | 3,5-di-t-butyl-4-hydroxyphenyl-O-CH₂-(3-chloro-4-cyanophenyl) |

EXAMPLE 15

Preparation of 5-[5-(3,5-Di-t-Butyl-4-hydroxyphenoxy)pentyl]tetrazole

Under a nitrogen atmosphere, a mixture of 3.79 g (0.012 mole) of 6-(3,5-di-t-butyl-4-hydroxyphenoxy)-hexanenitrile, 2.45 g (0.018 mole) of triethylammonium chloride, 2.31 g (0.036 mole) of sodium azide and 150 ml of N-methylpyrrolidinone was heated at about 150° C. for about 72 hours. The reaction mixture was cooled and poured into water. The aqueous mixture was acidified to pH 1 with 10% hydrochloric acid and then extracted six times with 100 ml portions of diethyl ether. The diethyl ether extracts were combined, dried over magnesium sulfate and evaporated to provide a yellow oil. This oil was purified by silica gel chromatography eluting with 2:1 hexane:acetone containing 3 drops of acetic acid per 2000 ml of solvent, followed by recrystallization from a mixture of ethyl acetate and hexane to provide 2.2 g of 5-[5-(3,5-di-t-butyl-4-hydroxyphenoxy)pentyl]tetrazole as an off-white crystalline solid, m.p. 140°–141° C. Analysis: Calculated for $C_{20}H_{32}N_4O_2$: %C, 66.6; %H, 8.95; %N, 15.5; Found: %C, 66.5; %H, 8.9; %N, 15.6.

EXAMPLES 16–18

Using the general method of Example 2, the indicated intermediates of Formula IV (Table II) could be converted to the tetrazoles of Formula I shown in Table II.

TABLE II

| Example No. | Starting Material | Product |
|---|---|---|
| 16 | 3,5-di-t-butyl-4-hydroxyphenyl-O-CH₂-(4-methyl-3-cyanophenyl) | 3,5-di-t-butyl-4-hydroxyphenyl-O-CH₂-(4-methyl-3-tetrazolylphenyl) |
| 17 | 3,5-di-t-butyl-4-hydroxyphenyl-O-CH₂-(4-methoxy-3-cyanophenyl) | 3,5-di-t-butyl-4-hydroxyphenyl-O-CH₂-(4-methoxy-3-tetrazolylphenyl) |

| Example No. | Starting Material | Product |
|---|---|---|
| 18 | (CH₃)₃C—C₆H₂(OH)(CH₃)₃C—O—CH₂—C₆H₃(Cl)—CN | (CH₃)₃C—C₆H₂(OH)(CH₃)₃C—O—CH₂—C₆H₃(Cl)—C(=N-NH-N=N) (tetrazole) |

EXAMPLE 19

Preparation of 5-[4-(3,5-Di-t-Butyl-4-hydroxyphenylthio)methyphenyl]tetrazole

A solution of 2.00 g (8.39 mmole) of the known compound 2,6-di-t-butyl-4-mercaptophenol, 1.65 g (8.39 mmole) of p-cyanobenzyl bromide, 5 ml of 1.68N sodium hydroxide and 75 ml of ethanol was heated at reflux for 48 hours. The reaction mixture was poured into water, and was then extracted with diethyl ether. The ether extract was washed with water, dried with magnesium sulfate and evaporated to give the crude product. This material was purified by silica gel chromatography, eluting with 1% ethyl acetate in hexane, followed by recrystallizations from a mixture of ethyl acetate and hexane and from ethanol to give 1.1 g of 2,6-di-t-butyl-4-[(4-cyanophenyl)methylthio]phenol as white needles, m.p. 143°–145° C. Analysis: Calculated for $C_{22}H_{27}NOS$: %C, 74.7; %H, 7.7; %N, 4.0; Found: %C, 75.1; %H, 8.1; %N, 4.1.

A mixture of 2.0g (0.011 mole) of 2,6-di-t-butyl-4-[(4-cyanophenyl)methylthio]phenol, 1.1 g (0.034 mole) of sodium azide, 0.6 g (0.034 mole) of ammonium chloride, 0.24 g (0.011 mole) of lithium chloride and 20 ml of N,N-dimethylformamide was heated at 115° C. in a stoppered flask for 120 hours. The N,N-dimethylformamide was evaporated and the residual material partitioned between water and chloroform. The chloroform layer was dried with magnesium sulfate, and was then evaporated to give the crude product as a brown oil. This oil was purified by silica gel chromatography eluting with a mixture of chloroform/methanol/acetic acid in a ratio of 98/2/0.25 followed by two recrystallizations from a mixture of chloroform and hexane to give 0.92 g of 5-{4-[(3,5-di-t-butylphenylthio)methyl]phenyl}tetrazole as a cream-colored solid, m.p. 187°–189° C. Analysis: Calculated for $C_{22}H_{28}N_4OS$: %C, 66.6; %H, 7.1; %N, 14.1; Found: %C, 66.6; %H, 7.3; %N, 14.3.

EXAMPLE 20

Preparation of 5-[3-(3,5-Di-t-Butyl-4-hydroxyphenylthiomethyl)-phenyl]tetrazole

A solution containing 2.00g (8.39 mmole) of 2,6-di-t-butyl-4-mercaptophenol, 1.65 g (8.39 mmole) of m-cyanobenzyl bromide, 5 ml of 1.68N sodium hydroxide and 75 ml of ethanol was heated at reflux for 48 hours. The reaction mixture was poured into water and was then extracted with diethyl ether. The ether extract was washed with water, dried with magnesium sulfate and evaporated to give the crude product. This material was purified by silica gel chromatography eluting with 1% ethyl acetate in hexane, followed by four recrystallizations from hexane to give 0.75g of 2,6-di-t-butyl-4-[(3-cyanophenyl)methylthio]phenol as white needles, m.p. 61°–63° C. Analysis: Calculated for $C_{22}H_{27}NOS$: %C, 74.7%; %H, 7.7; %N, 4.0; Found: %C. 74.5; %H, 8.0; %N, 3.8.

Three g (8.5 mmole) of 2,6-di-t-butyl-4-(3-cyanophenyl)methylthio]phenol, 1.65 g (25.5 mmole) of sodium azide, 1.36 g (25.5 mmole) of ammonium chloride, 0.36 g (8.5 mmole) of lithium chloride and 25 ml of N,N-dimethylformamide were combined and heated in a stoppered flask at 115° for 16 hours. To this mixture were added 1.65 g of sodium azide and 1.36 g of ammonium chloride, and the heating was continued for an additional 120 hours. The reaction mixture was poured into water and was then extracted with chloroform. The chloroform extract was dried with magnesium sulfate and was evaporated to give the crude product as an oil. This oil was purified by gel chromatography, eluting with a mixture of chloroformmethanol/acetic acid in a ratio of 98/2/0.25, followed by trituration with a mixture of chloroform and hexane and two recrystallizations from a mixture of ethanol and water to give 0.09g of white 5-[3-(3,5-di-t-butyl-4-hydroxyphenylthiomethyl)phenyl]tetrazole m.p. 177°–178° C. Analysis: Calculated for $C_{22}H_{28}N_4OS$: %C, 66.6; %H, 7.1; %N, 14.1; Found: %C, 66.4; %H, 7.1; %N 14.2.

EXAMPLE 21

Preparation of 2,6-Di-t-Butyl-4-[(2-cyanophenyl) methylthio]phenol

A solution of 2.00 g (8.39 mmole) of 2,6-di-t-butyl-4-mercaptophenol, 1.65 g (8.39 mmole) of o-cyanobenzyl bromide, 5 ml of 1.68N sodium hydroxide and 75 ml of ethanol was heated at reflux for 48 hours. The reaction mixture was poured into water and was extracted with diethyl ether. The ether extract was washed with water, dried with magnesium sulfate and evaporated to give the crude product as an oil. The oil was purified by silica gel chromatography, eluting with a mixture of ethyl acetate and hexane, followed by recrystallization from hexane to give 0.56 g of white 2,6-di-t-butyl-4-[(2-cyanophenyl) methylthio]phenol, m.p. 79°–82° C. Analysis: Calculated for $C_{22}H_{27}NOS$: %C, 74.7; %H, 7.7; %N, 4.0; Found: %C, 74.6; %H, 7.9; %N 3.6.

Using the general method of Example 19, the 2,6-di-t-butyl-4-[2-cyanophenyl)methylthio]phenol prepared above could be converted to 5-[2-(3,5-di-t-butyl-4-hydroxyphenylthiomethyl)phenyl]tetrazole.

EXAMPLE 22

Preparation of 4-(3,5-Di-t-Butyl-4-hydroxyphenylthiomethyl) benzoic Acid

A solution of 2.50 g (0.04 mole) of 90% potassium hydroxide in 10ml of water was added to a stirred solution containing 4.77 g (0.02 mole) of 2,6-di-t-butyl-4-mercaptophenol in 100 ml of ethanol. To the resulting light brown solution was added, in one portion, 4.30 g (0.02 mole) of 4-bromomethylbenzoic acid. The reaction was brought to reflux. After 30 minutes, 100 ml of ethanol was added to bring all material into solution. The reaction was refluxed for approximately 16 hours. The solvent was removed under vacuum and the residual oil was triturated with 100 ml of water. Acidification with 10% hydrochloric acid provided a solid which was collected, washed with water and air dried. This material was recrystallized first from a mixture of ethyl acetate and hexane and then from a mixture of ethanol and water to give 0.78 g of 4-(3,5-di-t-butyl-4-hydroxyphenylthiomethyl)benzoic acid as an off-white solid, m.p. 171°–174 C. Analysis: Calculated for $C_{22}H_{28}O_3S$: %C, 70.9, %H, 7.6 Found: %C, 71.2, %H, 7.6.

EXAMPLES 23–25

Nitrile intermediates of the invention of Formula IV which could be prepared by the reaction of 2,6-di-t-butyl-4-mercaptophenol with known starting materials of Formula III using the general method of Example 19 are shown in Table III. Using the general method of Example 19, the intermediates of Formula IV could be converted to the tetrazoles of the invention of Formula I which are also shown in Table III.

TABLE III

| Ex. No. | Starting Material of Formula III | Intermediate of Formula IV | Product of Formula I |
|---|---|---|---|
| 23 | 4-(bromomethyl)-2-methylbenzonitrile (CH₃ at para to CN, BrCH₂ at position, CN) | 4-((3,5-di-t-butyl-4-hydroxyphenylthio)methyl)-2-methylbenzonitrile | Corresponding tetrazole (CN replaced by tetrazole ring: N=N–NH–N=) |
| 24 | 4-(bromomethyl)-2-methoxybenzonitrile | 4-((3,5-di-t-butyl-4-hydroxyphenylthio)methyl)-2-methoxybenzonitrile | Corresponding tetrazole |
| 25 | 4-(bromomethyl)-2-chlorobenzonitrile | 4-((3,5-di-t-butyl-4-hydroxyphenylthio)methyl)-2-chlorobenzonitrile | Corresponding tetrazole |

EXAMPLES 26–30

Following the procedures of Example 22, the starting materials of Formula VII indicated in Table IV below could be reacted with 2,6-di-t-butyl-4-mercaptophenol to provide the indicated product of Formula VIII.

TABLE IV

| Example No. | Starting Material of Formula VII | Product of Formula VIII |
|---|---|---|
| 26 | 2-(bromomethyl)benzoic acid (BrCH₂–C₆H₄–CO₂H) | 2-((3,5-di-t-butyl-4-hydroxyphenylthio)methyl)benzoic acid |

TABLE IV-continued

| Example No. | Starting Material of Formula VII | Product of Formula VIII |
|---|---|---|
| 27 | CO₂H, BrCH₂–, OCH₃ (phenyl) | (CH₃)₃C, HO–, (CH₃)₃C – S–CH₂ – phenyl with CO₂H and OCH₃ |
| 28 | OCH₃, BrCH₂–, CO₂H (phenyl) | (CH₃)₃C, HO–, (CH₃)₃C – S–CH₂ – phenyl with OCH₃ and CO₂H |
| 29 | CO₂H, BrCH₂–, Cl (phenyl) | (CH₃)₃C, HO–, (CH₃)₃C – S–CH₂ – phenyl with CO₂H and Cl |
| 30 | CO₂H, BrCH₂–, Cl (phenyl) | (CH₃)₃C, HO–, (CH₃)₃C – S–CH₂ – phenyl with CO₂H and Cl |

EXAMPLE 31

Preparation of 5-(3,5-Di-t-Butyl-4-hydroxyphenoxy)valeronitrile

Under a nitrogen atmosphere, a solution of 10.0 g (0.045 mole) of 3,5-di-t-butyl-1,4-hydroquinone in 30 ml of N,N-dimethylformamide was added dropwise over a period of one hour to a suspension of 2.32 g (0.058 mole) of 60% sodium hydride in 20 ml of N,N-dimethylformamide. A solution of 9.39 g (0.058 mole) of 5-bromovaleronitrile in 5 ml of N,N-dimethylformamide was added dropwise and the resulting mixture was allowed to stir at about 25° C. for about 16 hours. The reaction mixture was poured into 150 ml of water and then extracted eight times with 100 ml portions of hexane. The extracts were combined, filtered through silica gel, dried over magnesium sulfate and then evaporated to provide 11.9 g of a yellow oil. The oil was purified by silica gel chromatography eluting with 10% ethyl acetate in hexane to provide 11.8 g of 5-(3,5-di-t-butyl-4-hydroxyphenoxy)valeronitrile as a white crystalline solid. The structure was confirmed by nuclear magnetic resonance spectral analysis.

EXAMPLE 32

Preparation of 5-[4-(3,5-Di-t-Butyl-4-hydroxyphenoxy)butyl]tetrazole

Under a nitrogen atmosphere, a mixture of 7.00 g (0.023 mole) of 5-(3,5-di-t-butyl-4-hydroxyphenoxy)valeronitrile, 4.73 g (0.034 mole) of triethylammonium chloride, 4,47 g (0.069 mole) of sodium azide and 200 ml of 1-methylpyrrolidone was heated at 150° C. for about 60 hours. The reaction mixture was cooled and then poured into 200 ml of water. The aqueous mixture was acidified to pH 1 with 10% hydrochloric acid and then extracted five times with 100 ml portions of diethyl ether. The diethyl ether extracts were combined, washed with brine, dried over magnesium sulfate and evaporated to provide an oil. The oil was purified by silica gel chromatography eluting with 2:1 hexane:acetone containing 3 ml of acetic acid per 1600 ml of solvent followed by recrystallization of the isolated material from a mixture of ethyl acetate and hexane to provide 3.3 g of 5-[4-(3,5-di-t-butyl-4-hydroxyphenoxy)butyl]tetrazole as a white solid, m.p. 141°–141.5° C. Analysis: Calculated for C₁₉H₃₀N₄O₂: %C, 65.9; %H, 8.7; %N, 16.2; Found: %C, 65.7; %H, 8.6; %N, 16.2.

What is claimed is:

1. A compound of the formula

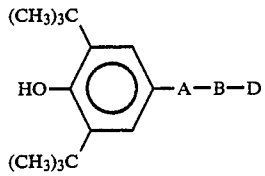

wherein A is an oxygen or sulfur atom; B is a straight chain alkylene group of 3 to 8 carbon atoms or

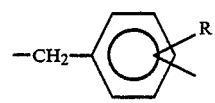

wherein R is hydrogen, halogen, lower alkyl or lower alkoxy; and D is carboxy or tetrazolyl; with the proviso that when A is sulfur, B is

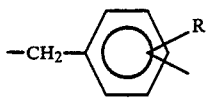

and, with the further proviso that when A is oxygen, D is tetrazolyl; or a derivative of a compound wherein D is carboxy selected from the group consisting of a lower alkyl ester, a (lower)alkylamino(lower)alkyl ester, a pharmaceutically acceptable lower(alkyl)amino(lower)alkyl ester acid addition salt, or a pharmaceutically acceptable carboxylate salt; or a derivative of a compound wherein D is tetrazolyl selected from a pharmaceutically acceptable alkali metal or alkaline earth salt of the tetrazolyl moiety.

2. A compound according to claim 1, wherein A is an oxygen atom.

3. A compound according to claim 2, wherein B is said alkylene group.

4. A compound according to claim 2, wherein B is said

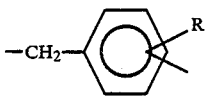

group.

5. 5-[4-(3,5-di-t-butyl-4-hydroxyphenoxymethyl)phenyl]tetrazole or a pharmaceutically acceptable alkali metal or alkaline earth salt thereof according to claim 1.

6. 5-[6-(3,5-di-t-butyl-4-hydroxyphenoxy)hexyl]tetrazole or a pharmaceutically acceptable alkali metal or alkaline earth salt thereof according to claim 1.

7. 5-[2-(3,5-di-t-butyl-4-hydroxyphenoxymethyl) phenyl]tetrazole or a pharmaceutically acceptable alkali metal or alkaline earth salt thereof according to claim 1.

8. 5-[3-(3,5-di-t-butyl-4-hydroxyphenoxy)propyl]tetrazole or a pharmaceutically acceptable alkali metal or alkaline earth salt thereof according to claim 1.

9. 5-[3-(3,5-di-t-butyl-4-hydroxy-phenoxymethyl)phenyl]tetrazole or a pharmaceutically acceptable alkali metal or alkaline earth salt thereof according to claim 1.

10. 5-[5-(3,5-di-t-butyl-4-hydroxy)pentyl]tetrazole or a pharmaceutically acceptable alkali metal or alkaline earth salt thereof according to claim 1.

11. 5-[4-(3,5-di-t-butyl-4-hydroxyphenoxy)-butyl]tetrazole or a pharmaceutically acceptable alkali metal alkaline earth salt thereof according to claim 1.

12. A compound according to claim 1, wherein A is a sulfur atom.

13. A compound according to claim 12, wherein D is carboxy.

14. A compound according to claim 12, wherein D is tetrazolyl.

15. 5-[4(3,5-di-t-butyl-4-hydroxyphenylthio)methylphenyl]tetrazole or a pharmaceutically acceptable alkali metal or alkaline earth salt thereof according to claim 1.

16. 5-[3-(3,5-di-t-butyl-4-hydroxyphenylthiomethyl)phenyl]tetrazole or a pharmaceutically acceptable alkali metal or alkaline earth salt thereof according to claim 1.

17. 4-(3,5-di-t-butyl-4-hydroxyphenylthiomethyl)benzoic acid or a said derivative thereof according to claim 1.

18. An antiallergic pharmaceutical composition comprising a compound according to claim 1 and a pharmaceutically acceptable vehicle, said compound being present in an amount effective to inhibit an allergic condition.

19. An antiallergic pharmaceutical composition according to claim 18, wherein A of said compound is an oxygen atom.

20. An antiallergic pharmaceutical composition according to claim 18, wherein A of said compound is a sulfur atom.

21. A method for inhibiting bronchoconstriction in a mammal wherein a compound according to claim 1 is administered to said mammal in an amount sufficient to inhibit bronchoconstriction.

22. A method according to claim 21, wherein said compound is administered orally.

23. A method for inhibiting leukotriene biosynthesis in a mammal comprising administering to said mammal a compound according to claim 1 in an amount effective to inhibit said biosynthesis.

* * * * *